(12) United States Patent
Merkin

(10) Patent No.: US 10,665,333 B2
(45) Date of Patent: May 26, 2020

(54) SYSTEMS AND METHODS FOR ASSESSING AND OPTIMIZING HEALTHCARE ADMINISTRATION

(71) Applicant: Richard Merkin, Marina Del Rey, CA (US)

(72) Inventor: Richard Merkin, Marina Del Rey, CA (US)

(*) Notice: Subject to any disclaimer, the term of this patent is extended or adjusted under 35 U.S.C. 154(b) by 633 days.

(21) Appl. No.: 14/632,174

(22) Filed: Feb. 26, 2015

(65) Prior Publication Data

US 2015/0169831 A1 Jun. 18, 2015

Related U.S. Application Data

(63) Continuation of application No. 14/227,307, filed on Mar. 27, 2014, now abandoned, and a continuation of application No. 13/969,838, filed on Aug. 19, 2013, now abandoned, and a continuation of application No. 12/834,767, filed on Jul. 12, 2010, now
(Continued)

(51) Int. Cl.
| | |
|---|---|
| *G16H 10/60* | (2018.01) |
| *G16H 50/70* | (2018.01) |
| *G16H 15/00* | (2018.01) |
| *G06Q 50/22* | (2018.01) |
| *G06Q 50/24* | (2012.01) |
| *G16H 40/20* | (2018.01) |

(52) U.S. Cl.
CPC ............ *G16H 10/60* (2018.01); *G06Q 50/22* (2013.01); *G06Q 50/24* (2013.01); *G16H 15/00* (2018.01); *G16H 40/20* (2018.01); *G16H 50/70* (2018.01)

(58) Field of Classification Search
CPC .. G06F 19/327; G06F 19/322; G06F 19/3443; G06F 19/3487; G06Q 50/22; G06Q 50/24
USPC .......................................................... 705/2–3
See application file for complete search history.

(56) References Cited

U.S. PATENT DOCUMENTS

| | | | |
|---|---|---|---|
| 5,544,044 A | 8/1996 | Leatherman | |
| 5,652,842 A * | 7/1997 | Siegrist, Jr. ............ | G06Q 40/02 345/440 |

(Continued)

*Primary Examiner* — Eliza A Lam
(74) *Attorney, Agent, or Firm* — Stetina Brunda Garred and Brucker

(57) ABSTRACT

A comprehensive patient data assessment system and method for use in generating, tracking and analyzing medical data related to healthcare administered by a group of physicians to a specified patient population. The system is operative to track data related to the claims history, case management, pharmacy data, and lab tests/results for each patient treated by each patient's primary care physician preferably through electronic medical records that are accessible over a computer network. The system is operative to generate data indicative of the utilization of healthcare resources utilized to treat each patient within the patient population, as well as ensure that each primary care physician utilizes appropriate codes for each diagnosis and procedure/test administered to each patient. The system further provides for categorization of patients afflicted with chronic conditions that require high-cost care. The systems are exceptionally effective in conserving medical resources, ensuring uniformity in administering healthcare, and achieving optimal patient outcomes.

4 Claims, 11 Drawing Sheets

Related U.S. Application Data abandoned, and a continuation of application No. 11/063,268, filed on Feb. 22, 2005, now abandoned.

(56) References Cited

U.S. PATENT DOCUMENTS

| | | | |
|---|---|---|---|
| 5,835,897 A * | 11/1998 | Dang | G06F 19/328 705/2 |
| 5,970,463 A * | 10/1999 | Cave | G06F 19/322 705/2 |
| 6,047,259 A | 4/2000 | Campbell et al. | |
| 6,067,524 A | 5/2000 | Byerly | |
| 6,240,394 B1 | 5/2001 | Uecker | |
| 6,341,265 B1 | 1/2002 | Provost | |
| 6,343,271 B1 | 1/2002 | Peterson et al. | |
| 6,735,569 B1 | 5/2004 | Wizig | |
| 6,820,058 B2 | 11/2004 | Wood et al. | |
| 6,824,052 B2 | 11/2004 | Walsh | |
| 7,016,856 B1 | 4/2006 | Wiggins | |
| 7,039,458 B2 | 5/2006 | Ueda et al. | |
| 2001/0037214 A1 | 11/2001 | Raskin et al. | |
| 2002/0007290 A1 | 1/2002 | Gottlieb | |
| 2002/0019754 A1 | 2/2002 | Peterson et al. | |
| 2002/0026105 A1 | 2/2002 | Drazen | |
| 2002/0035316 A1 | 3/2002 | Drazen | |
| 2002/0120471 A1 | 4/2002 | Drazen | |
| 2002/0062226 A1 | 5/2002 | Ito | |
| 2002/0149616 A1 | 10/2002 | Gross et al. | |
| 2003/0069760 A1 * | 4/2003 | Gelber | G06Q 40/02 705/4 |
| 2003/0074228 A1 | 4/2003 | Walsh | |
| 2003/0078811 A1 | 4/2003 | Cole et al. | |
| 2003/0078813 A1 | 4/2003 | Haskell et al. | |
| 2003/0078911 A1 | 4/2003 | Haskell et al. | |
| 2004/0153337 A1 * | 8/2004 | Cruze | G06F 19/328 705/2 |
| 2004/0186744 A1 | 9/2004 | Lux | |
| 2006/0080146 A1 | 4/2006 | Cook et al. | |
| 2006/0085222 A1 | 4/2006 | Huang et al. | |
| 2014/0214453 A1 | 7/2014 | Merkin | |

* cited by examiner

High Cost Chronic Condition

Cancer [HCC: 10,8,9,7]
Breast, Prostate, Colorectal and Other Cancers and Tumors [HCC: 10]
Lung, Upper Digestive Tract, and Other Severe Cancers [HCC: 8]
Lymphatic, Head and Neck, Brain, and Other Major Cancers [HCC: 9]
Metastatic Cancer and Acute Leukemia [HCC: 7]

Cardiovascular Disease [HCC: 81,80,92,82]
Acute Myocardial Infarction [HCC: 81]
Congestive Heart Failure [HCC: 80]
Specified Heart Arrhythmias [HCC: 92]
Unstable Angina and Other Acute Ischemic Heart Disease [HCC: 82]

Diabetes [HCC: 17,16,18,15,19]
Diabetes with Acute Complications [HCC: 17]
Diabetes with Neurologic or Other Specified Manifestation [HCC: 16]
Diabetes with Ophthalmologic or Unspecified Manifestation [HCC: 18]
Diabetes with Renal or Peripheral Circulatory Manifestation [HCC: 15]
Diabetes without Complication [HCC: 19]

Dialysis Condition [HCC: 130,132,131]
Dialysis Status [HCC: 130]
Nephritis [HCC: 132]
Renal Failure [HCC: 131]

HIV/Opportunistic Infections [HCC: 1,5,112]
HIV/AIDS [HCC: 1]
Opportunistic Infections [HCC: 5]
Pneumococcal Pneumonia, Empyema, Lung Abscess [HCC: 112]

Liver Disease [HCC: 27,26,25]
Chronic Hepatitis [HCC: 27]
Cirrhosis of Liver [HCC: 26]
End-Stage Liver Disease [HCC: 25]

Pulmonary Disease [HCC: 108]
Chronic Obstructive Pulmonary Disease [HCC: 108]

Quadriplegia/Other Extensive Paralysis [HCC: 101,100,68,67,69,157]
Cerebral Palsy and Other Paralytic Syndromes [HCC: 101]
Hemiplegia/Hemiparesis [HCC: 100]
Paraplegia [HCC: 68]
Quadriplegia/Other Extensive Paralysis [HCC: 67]
Spinal Cord Disorders/Injuries [HCC: 69]
Vertebral Fractures without Spinal Cord Injury [HCC: 157]

Fig. 5

Current Diagnosis Code Which May Require Further Coding

Please select a chronic condition to review:

- Cancer
- Cardiovascular Disease
- Diabetes
- Dialysis Condition
- ESRD
- HIV/Opportunistic Infections
- Liver Disease
- Pulmonary Disease
- Quadriplegia/Other Extensive Paralysis

Fig. 6

Current Diagnosis Code Which May Require Further Coding
Chronic condition: Cancer

- Did member undergo active treatment for colon cancer during the data collection period?

- Did member undergo active treatment for colorectal cancer during the data collection period?

- Did member undergo active treatment for head and neck cancer during the data collection period?

- Did member undergo active treatment for laryngeal carcinoma during the data collection period?

- Did member undergo active treatment for lung carcinoma during the data collection period?

- Did member undergo active treatment for malignant melanoma during the data collection period?

- Does medical record contain documentation of active treatment for malignant neoplasm of mouth, tongue, salivary glands, pharynx, esophagus, etc.

- Does medical record contain documentation of active treatment for pulmonary or disseminated mycobacteria?

- Has patient been actively managed for any malignant neoplasm?

- If patient has a malignant neoplasm of other urinary organs, then additional coding is warranted.

- If patient has a malignant neoplasm of the female genital organs, then additional coding is warranted.

- If patient has a malignant neoplasm of the prostate, then additional coding is warranted.

- If patient has malignant breast cancer, then additional coding is warranted

Fig. 7

Current Diagnosis Code Which May Require Further Coding
Chronic condition: Cardiovascular Disease

- Does patient have history of MI or angina documented on EKG or other special study, even if asymptomatic? EKG evidence of old MI

- Does patient have prior history of cardiopulmonary disorder predisposing to current cardiac issues?

- Does patient meet clinical criteria for cardiomypathy?

- Has patient been actively managed for third degree AV block?

- More specific coding is necessary for atrial or ventricular arrhythmia

- Was patient receiving active treatment for chronic renal failure, chronic uremia, unspecified renal sclerosis, heart failure, myocardial degeneration or myocarditis during the risk assessment period?

- Was patient receiving active treatment for heart failure, myocardial degeneration or myocarditis during the risk assessment period?

Fig. 8

Current Diagnosis Code Which May Require Further Coding
Chronic condition: Dialysis Condition

- Was patient receiving active treatment for chronic renal failure, chronic uremia, or unspecified renal sclerosis during the risk assessment period?

- Was patient receiving active treatment for chronic renal failure, chronic uremia, unspecified renal sclerosis, heart failure, myocardial degeneration or myocarditis during the risk assessment period?

Fig. 9

Current Diagnosis Code Which May Require Further Coding
Chronic condition: HIV/Opportunistic Infections

- Does medical record contain documentation of active treatment for candidal pneumonia or systemic candidiasis?

- Does medical record contain documentation of active treatment for HIV-2 retrovirus?

- Does medical record contain documentation of active treatment for infection by aspergillus species, crytococcosis or Zygomycosis?

- Does medical record contain documentation of active treatment for pumonary coccidioidomycosis?

Fig. 10

Review for Potential Additional Related Diagnosis
Based on Current Diagnosis

- Cancer
    - Members with HCC 8 to be reviewed for potential HCC 7
    - Members with HCC 9 to be reviewed for potential HCC 7 and 8
    - Members with HCC 10 to be reviewed for potential HCC 7 and 8 and 9

- Cardio
    - Members with HCC 82 to be reviewed for potential HCC 81

- Diabetes
    - Members with HCC 16 to be reviewed for potential HCC 15
    - Members with HCC 17 to be reviewed for potential HCC 15 and 16
    - Members with HCC 18 to be reviewed for potential HCC 15 and 16 and 17
    - Members with HCC 19 to be reviewed for potential HCC 15 and 16 and 17 and 18

- Dialysis
    - Members with HCC 131 to be reviewed for potential HCC 130
    - Members with HCC 132 to be reviewed for potential HCC 130 and 131

- HIV
    - Members with HCC 112 to be reviewed for potential HCC 5 and 111

- Liver
    - Members with HCC 26 to be reviewed for potential HCC 25
    - Members with HCC 27 to be reviewed for potential HCC 25 and 26

- Pulmonary
    - Members with HCC 108 to be reviewed for potential HCC 107

- Quadriplegia
    - Members with HCC 68 to be reviewed for potential HCC 67
    - Members with HCC 69 to be reviewed for potential HCC 67 and 68
    - Members with HCC 100 to be reviewed for potential HCC 67 and 68
    - Members with HCC 101 to be reviewed for potential HCC 67 and 68 and 100
    - Members with HCC 157 to be reviewed for potential HCC 67 and 68 and 69

Fig.11

SYSTEMS AND METHODS FOR ASSESSING AND OPTIMIZING HEALTHCARE ADMINISTRATION

CROSS-REFERENCE TO RELATED APPLICATIONS

The present application is a continuation of U.S. patent application Ser. No. 14/227,307 filed on Mar. 27, 2014, which is a continuation of U.S. patent application Ser. No. 13/969,838 filed Aug. 19, 2013, now abandoned, which is a continuation of U.S. patent application Ser. No. 12/834,767 filed Jul. 12, 2010, now abandoned, which is a continuation of U.S. patent application Ser. No. 11/063,268 filed Feb. 22, 2005, now abandoned.

STATEMENT RE: FEDERALLY SPONSORED RESEARCH/DEVELOPMENT

Not Applicable

BACKGROUND OF THE INVENTION

The present invention is directed to systems and methods for comprehensively assessing and optimizing the administration of healthcare as rendered by a group of physicians to a specific patient population. More particularly, the present invention comprises systems and methods that conserve medical resources utilized to care for the patient population, ensure uniformity in the procedures/tests utilized to render such care, identify and assess those patients afflicted with a chronic condition requiring high-cost healthcare, and provide means to continuously monitor and evaluate the quality of healthcare delivered.

Essential to high quality and cost-effective health care is the proper diagnosis of a patient's condition. From a proper diagnosis, the appropriate medical attention utilized to treat the underlying condition, whether it be the performance of a medical procedure, laboratory tests and/or prescription of medication, can be determined. To that end, and as is well-known in the art, standard diagnoses codes are extensively utilized pursuant to conventional disease classification techniques that provide a quick, well-understood method to document medical care administered to a patient. Exemplarily of and perhaps most widely utilized of such formats is the International Classification of Diseases $9^{th}$ Edition (ICD number 9) three digit codes. Likewise, with respect to the medical treatment that has been rendered, such procedures are typically referenced according to Current Procedural Terminology (CPT). Also frequently referenced in connection with the delivery of health care are drug codes (e.g., NDC), other service codes (e.g., HCPCS), among others.

Notwithstanding such basic principles of medicine, as well as an infrastructure of coding practices to help facilitate the delivery of health care and documentation of patient treatment, the current administration of healthcare in the United States is subject to tremendous abuse and is grossly inefficient. In this regard, patients, healthcare providers and healthcare providing institutions often encourage wasteful practices that result in needless procedures and tests being performed. Moreover, healthcare providers and healthcare providing institutions, such as hospitals, clinical laboratories, outpatient and rehabilitation facilities, engage in capricious billing practices that enable such providers and institutions to charge for a multiplicity of services that may be available under a single clinical event that is typically identified by a single CPT code.

Further problematic with such practice is that healthcare providers and healthcare providing institutions frequently utilize the wrong codes for diagnosis or otherwise use incorrect or multiple CPT codes to seek reimbursement, whether it be from an insurance company, health maintenance organization or government sponsored healthcare program, such as Medicare. In this regard, by failing to follow any type of uniform healthcare delivery system, and hence uniform coding practice commensurate therewith, results in overcharges for procedures that have been unnecessarily performed, improper diagnosis and duplicative and unnecessary tests and procedures.

In addition to health care providers and institutions, patients themselves contribute substantially to the cost and ineffective utilization of health care resources. As is well-known, patients can and frequently do seek unnecessary medical treatment or otherwise attempt to influence the judgment of the health care provider by demanding that unnecessary tests or procedures be performed, that the patients have access to specialists or particular medications, and/or seek in-patient services in situations where the patient's clinical condition clearly does not justify such level of care. Such potential abuses are particularly likely where patients are allowed the discretion to directly access specialists, as is typical in several well-known health care insurance plans, such as Blue Cross and Blue Shield, which thus bypasses the critical role played by the primary care physician in making an initial assessment of a patient's condition and whether the same truly warrants the attention of a particular specialist, and not to mention the specialist best suited to handle a particular condition.

Such conventional health care practices are particularly wasteful in the context of providing healthcare to patients afflicted with a chronic condition requiring aggressive medical management. Such conditions, known as high-cost chronic conditions, include cancer, cardiovascular disease, diabetes, HIV, liver disease and pulmonary disease, among several others. To treat such high-cost chronic conditions typically involves continuous patient treatment, which may take the form of a variety of medical procedures, tests, prescription medicines, and the like, as well as continuously monitoring the patient's condition to make sure that the underlying chronic condition does not develop to a more advance state, develop complications, and/or give rise to further related medical condition. Current practices, however, are ill suited to dynamically treat the progression of disease, and most physicians and healthcare institutions merely react to the patient's condition as opposed to be proactively involved in and anticipate the potential future needs of the patient. Such lack of responsiveness is typically reflected in the coding practices associated with the care delivered to the patient, which often times can be inaccurate and inappropriate based upon a general lack of patient history documentation and anticipated need to follow up with the patient. As a result of such poor practices, medical costs associated with the treatment of chronic conditions become astronomical and almost always beyond the capability of most individuals to pay.

In order to counter such wasteful and abusive practices, attempts have been made to implement certain procedures to contain health care costs and conserve the utilization of health care resources. Exemplary of such attempts include requiring prior authorization and approval by an intermediate entity, such as a health maintenance organization or health insurance plan, to the extent a physician seeks to take a specified action, such as perform surgery, order a medical supply or refer the patient to a specialist. Also utilized are the practices of bundling, whereby a physician is paid a single payment for two or more medical services, and capitation whereby a health care provider is paid a set dollar amount as determined by a per member, per month calculation to deliver medical services to a specific patient population (i.e., members of a health maintenance organization). Still further examples include the use of preferred provider discounts, which encourage the use by patients of specific health care providers, and usual and customary reductions, which impose a reduction in the payment of medical services rendered as deemed justified by a health plan or insurance company based upon what is considered to be the justified value of such services as rendered in a particular geographical area.

Despite such attempts, however, there has yet to be devised any type of health care administration system or method that substantially conserves utilization of health care resources that, as a consequence, can dramatically lower the costs associated with providing care to a specific patient population, especially in connection with the treatment of patients with high cost chronic conditions. Such attempts have likewise failed to maintain any degree of consistent quality of health care insofar as prior art cost containment practices have been and continue to be riddled with "loopholes" with insufficient cost-deterrent mechanisms necessary to conserve and optimally utilize a finite amount of health care resources to treat accurately diagnosed patients.

As a result of the aforementioned abuses and inefficiencies associated with the utilization of health care resources, the cost of health care has and continues to increase substantially while the quality of the health care provided has not necessarily improved. As such, there is a substantial need in the art for a health care administration system and method that are operative to effectively and efficiently utilize health care resources to administer care to a patient population as compared to conventional practices. There is additionally a need for a healthcare administration system and method that utilizes a standardized coding practice that adheres to a standardized diagnosis treatment scheme that can be reviewed for accuracy and physician competency. There is still further a need in the art for such a system and method that is generally effective in eliminating the wasteful practices associated with the allocation and utilization of health care resources, especially in connection with the treatment of patients affected with chronic ailments, without adversely compromising clinical outcomes or quality of care.

BRIEF SUMMARY OF THE INVENTION

The present invention specifically addresses and alleviates the above-identified deficiencies in the art. In this regard, the present invention is directed to a comprehensive medical information and treatment system that is operative to compile, track and provide means for reviewing the administration of healthcare by a group of physicians and healthcare administration institutions to a specific patient population. In this respect, the present invention is operative to assess the appropriateness of each and every diagnosis, as well as the specific tests and procedures that have been ordered/rendered by a primary care physician to specific patients within the patient population. The system specifies, through a uniform coding procedure, each diagnosis and every test/procedure ordered/rendered by each physician for each patient such that a comprehensive medical history is compiled for each patient. The system further tracks each event for which medical care was rendered (claims history), the patient's case management, pharmacy information related to all medications prescribed to the patient, and any and all laboratory tests and results therefrom, including the specific dates that such procedures and tests were performed and medications prescribed. The compiled data will preferably be managed as electronic medical records accessible through a computer network, and in particular the Internet.

From such compilation of data, an assessment is made according to standardized care criteria and coding practices whereby a specific physician can be assessed as to the appropriateness of the diagnosis made, as well as the care he or she has rendered based upon the specific procedures and tests that were rendered/ordered to the specific patients under his of her care. In this regard, it is contemplated that the competency and efficiency by which a specific physician practices medicine can be adjudged according to the appropriateness of the coding practices followed by the physician, which will correlate with the proper diagnosis and specific type of procedures and tests administered to specific patients on specific occasions. Along these lines, it is contemplated that a number of statistical analyses can be applied in reviewing the electronic medical records that are operative to assess potentially inappropriate coding practices, which are thus indicative of wasteful, unnecessary or sub-optimal healthcare.

In addition to the foregoing compilation and assessment of healthcare as administered by a select group of physicians to a specific patient population, the system further integrates data related to the diagnosis and treatment associated with the care of patients within the patient population afflicted with high-cost chronic conditions, such as cancer, cardiovascular disease, diabetes, pulmonary disease or quadriplegia. The system is further particularly sensitive with respect to the treatment of high-cost chronic conditions in order to ensure that such chronic conditions have been properly diagnosed, whether further coding (indicative of further specific procedures and tests) may be warranted, whether additional coding is appropriate based upon additional related diagnoses based upon the current diagnosis (potential hierarchical review), and review to ensure that the treating physician has complied with all proper coding procedures indicative of the most cost-effective medical management practices coupled with the most favorable patient outcome.

With regard to those patients that have been properly identified as being afflicted with a high-cost chronic condition, the system of the present invention is operative to separately compile data related thereto to thus enable those patients to be assessed based upon the type of condition and required long-term treatment necessary to secure the most favorable patient outcome. Additionally, such information associated with those members having a high-cost chronic condition can be utilized to develop cost-effective treatment strategies that may be custom tailored to provide an optimal patient treatment.

In addition to the foregoing, it is further contemplated that by virtue of existing preferably in an electronic medical record format, the systems and methods of the present invention will be exceptionally useful in performing standardized electronic transactions as provided for in the Health Insurance Portability and Accountability Act (HIPAA) of 1996. In this regard, such transactions, as set forth in HIPAA, expressly include claims, remittance and payment advice, claims status, enrollment and disenrollment in a health plan, premium payments, eligibility inquiries and responses, referral certifications and authorizations, coordination of benefits, and the like, all of which can be facilitated through use of the present invention according to a standardized transaction format, which can include the uniform use of codes typically associated with conventional billing practices, such as diagnosis codes mentioned above (i.e., ICDM-9-CM, CPT-4, NDC, and HCPCS).

All of these objectives and more are accomplished by the present invention.

BRIEF DESCRIPTION OF THE DRAWINGS

These, as well as other features of the present invention, will become more apparent upon reference to the drawings wherein:

FIG. 5 is a list of high-cost chronic conditions that further includes specific sub-categories of such high-cost chronic conditions wherein each sub-category diagnosis is assigned a specific HCC code.

FIG. 6 is a listing of the high-cost chronic conditions of FIG. 5 that are identified as possibly requiring further coding with respect to additional medical procedures and tests that may be essential to provide care for a patient afflicted with a high-cost chronic condition.

FIG. 7 is a list of medical factors and questions to be taken into consideration by a physician when treating a patient properly diagnosed with cancer.

FIG. 8 is a list of medical factors and questions to be taken into consideration by a physician when treating a patient properly diagnosed with cardiovascular disease.

FIG. 9 is a list of medical factors and questions to be taken into consideration by a physician when treating a patient properly diagnosed with dialysis condition.

FIG. 10 is a list of medical factors and questions to be taken into consideration by a physician when treating a patient properly diagnosed with HIV/opportunistic infections.

FIG. 11 is a listing of potential additional related diagnoses that a physician must take into consideration when treating a patient having been diagnosed with a specific high-cost chronic condition.

DETAILED DESCRIPTION OF THE INVENTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Figure 1:
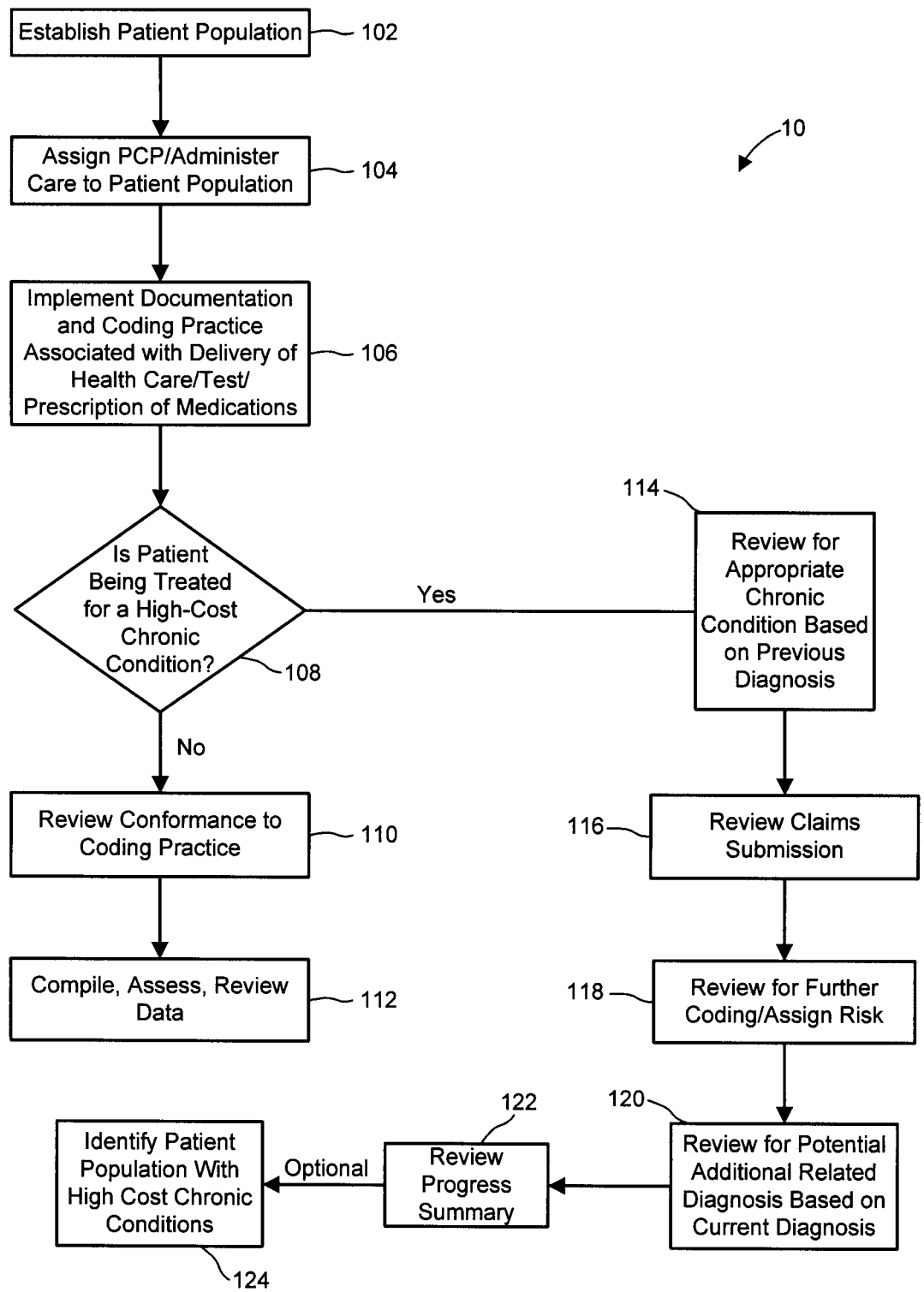
FIG. 1 is a flowchart depicting the steps for practicing the present invention as it relates to administering and documenting healthcare administered by primary care physicians to a patient population, including healthcare administered to patients within the patient population afflicted with high-cost chronic conditions.

Referring now to FIG. 1, there is schematically illustrated the various steps by which the system and method of the present invention 10 operate to generate data related to the delivery of healthcare to a patient population and how such delivery of healthcare can be optimized. To that end, it is contemplated that the present invention will be utilized exclusively by healthcare providers, which includes physicians, hospitals, medical groups, healthcare plans, health maintenance organizations, or any entity that provides healthcare to a patient population.

To create such framework, a patient population is first established 102 to which healthcare will be provided. To that end, it is contemplated that the identification of the patient population may take any of a variety of forms well-known in the art, including the teachings of Applicant's co-pending patent applications U.S. patent application Ser. No. 10/615, 640, filed Jun. 8, 2003 entitled HEALTHCARE ADMINISTRATION METHOD and U.S. patent application Ser. No. 10/679,178 entitled HEALTHCARE ADMINISTRATION METHOD HAVING QUALITY ASSURANCE, filed on Oct. 3, 2003, each of which are expressly incorporated herein by reference.

To care for such patient population, there is further provided a network or infrastructure of healthcare providers and healthcare providing institutions that will preferably comprise an integrated medical delivery system consisting of physicians and in-patient and out-patient facilities capable of comprehensively delivering medical treatment to those patients within the patient population. In this respect, and as per the teachings of Applicant's aforementioned pending patent applications, the present invention relies upon a procedural framework whereby primary care physicians are responsible for the initial assessment, diagnosis and treatment of those patients within the patient population seeking treatment. Moreover, for reasons discussed more fully below, such primary care physicians (PCP's) are further obligated to closely adhere to a strict coding procedure that accurately and efficiently standardizes medical diagnosis and, based upon such diagnosis, helps dictate what medical services, both short term and, where applicable, long term, are to be rendered in relation to a specific patient's condition.

To that end, and in order to deliver healthcare to patients within the patient population, primary care physicians (PCP's) will be assigned to patients within the patient population via 104 and will be primarily responsible for administering care thereto. With respect to such arrangements, it is contemplated that any of a variety of well-known techniques and healthcare practices known in the art can be utilized, such as those established by insurance carriers, health maintenance organizations, and the like are made available to patients within the patient population to access for treatment. In this respect, it is contemplated that conventional office-based appointments/doctors visits will be coordinated between patients in the patient population and their respective PCP's according to conventional practice.

Key to the practice of the present invention occurs in step 106, which is implemented every time a PCP treats a patient within the patient population. According to such step, significant documentation will be obtained in relation to the nature of medical care administered to a patient by a PCP, or other specialist as may be required, as discussed more fully below in relation to FIGS. 2-4. To that end, it is expressly contemplated that the systems and methods of the present invention will incorporate the use of electronic medical records that are operative to facilitate the input, storage, retrieval, transfer and review of medical information to other entities involved in the delivery of healthcare to patients within the patient population, including hospitals, in-patient and out-patient facilities, labs, insurance carriers, physicians offices, and the like. Exemplary of certain lesser-preferred formats operative to generate electronic medical records include medical record software produced by American Medical Software of Edwardsville, Ill.; Smart Doctor EMR, produced by Intelligent Medical Systems, Inc. of Alpine, Tex.; SOAPware EMR Software produced by Docs, Inc. of Springdale, Ariz.; and EMR Medical Software produced by Expert System Applications, Inc. of Solon, Ohio.

In a preferred embodiment, the medical records generated electronically through the preferred practice of the present invention will be accessible over the Internet or through secure intranet computer networks well-known to those skilled in the art. Exemplary of a most-preferred implementation of the systems and methods of the present invention include proprietary medical data management the website http://www.hmshcc.com operated by Heritage Medical Systems of Reseda, Calif. As will be readily understood by those skilled in the art, by providing a web-based system greatly facilitates access to medical records, as well as is operative to provide secure means by which such data can be generated, stored, retrieved and reviewed.

Given the electronic medical record format by which the delivery of healthcare will be documented according to step 106, there will further be implemented a coding practice associated with the delivery of such healthcare. The documentation and coding practice will preferably be consistent with the schematics as set forth in FIGS. 2-4.

Figure 2:
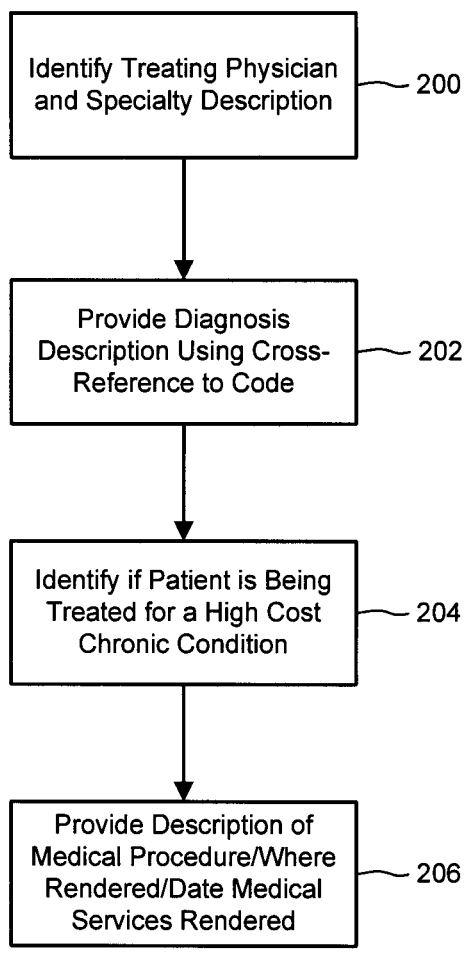
FIG. 2 is a flowchart depicting information obtained in order to generate a claims history for each incident medical care is rendered to a patient within the patient population.

With reference to FIG. 2, there is shown a first area of data to be collected in connection with the treatment of a specific patient within the patient population by the patient's PCP. Such information is directed to the creation and documentation of a claims history. To that end, for each incident for which medical care is rendered, there will be documented the identity of the treating physician 200 and a specialty description of that physician, and whether or not the same is the patient's PCP or otherwise a medical specialist. A diagnosis will further be identified in 202 that, for reasons discussed more fully below, will be consistent with a conventional coding practice, such as ICD-9-CM, well-known to those skilled in the art. Of substantial significance, and likewise discussed more fully below in connection with step 108, is whether or not the diagnosis involves a high-cost chronic condition determined in step 204, which if accurate, is operative to trigger a comprehensive on-going medical assessment that ensures that all aspects of the patient's condition are adequately reviewed and considered when implementing treatment.

In response to the identified diagnosis made in 202, documentation is further obtained with respect to the specific medical procedure that was rendered to treat such condition in step 206, as well as where such services were rendered, whether it be a hospital, in-patient or out-patient facility, and the date the medical services were rendered. To facilitate the input of such information, it is contemplated that the description of the medical procedures as performed may be consistent with the use of conventional CPT codes, such as CPT-4 and other service codes, such as HCPCS, among others. Key with the identification of the description of the medical procedure/services rendered will be an assessment as to how the same were effective and appropriate in treating the condition diagnosed.

Figure 3:
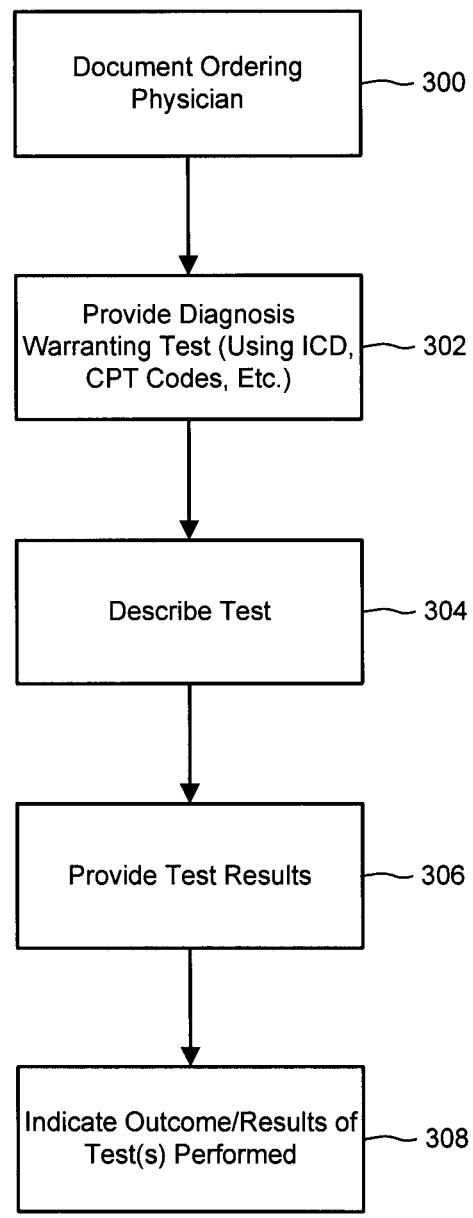
FIG. 3 is a flowchart depicting the steps for obtaining information relating to all laboratory tests performed for each patient within the patient population, as well as the results of such tests.

In addition to the claims history information generated as part of the implementation of the documentation and coding practice of step 106 of FIG. 1 and sub-steps 200-206 of FIG. 2, is the documentation of all lab results for each service provided to each patient. With respect to the documentation of such information, there is depicted in FIG. 3 the information that should necessarily be obtained in connection with any tests ordered in connection with the treatment of a specific patient within the patient population. As illustrated, the physician ordering the specific tests should be documented 300, along with the physician's diagnosis warranting the specific tests 302. To that end, it is contemplated that standardized diagnoses and procedure/service codes can be utilized. It is further preferred that a description of the lab test be provided 304 as well as the results of the prescribed tests 306. Where applicable, to the extent information regarding specific tests has some type of clinically meaningful outcome, the same should be indicated in 308. It is further contemplated that the dates of such tests are rendered likewise be documented as part of step 308.

Figure 4:
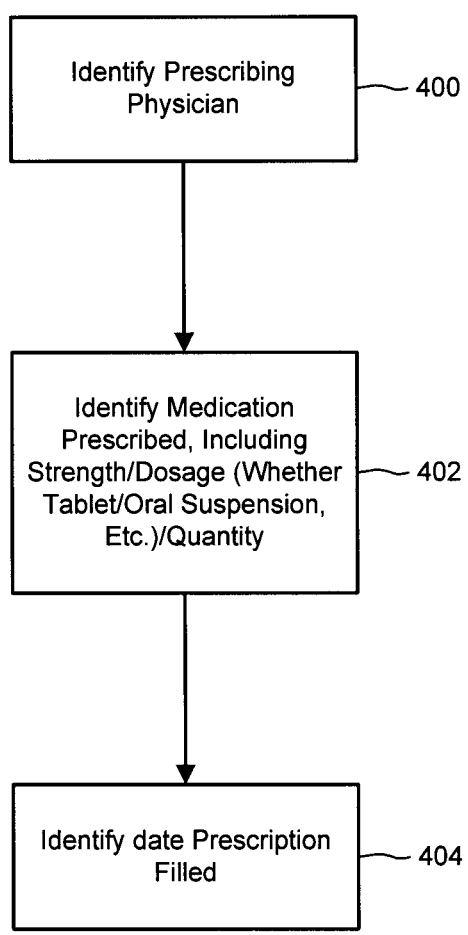
FIG. 4 is a flowchart depicting information to be obtained in connection with pharmacy data/prescription information for each medication prescribed to each patient within the patient population.

As a further component of the documentation and coding practice implemented in connection with the delivery of healthcare set forth in step 106 of FIG. 1, there is shown in FIG. 4 the documentation to be obtained in connection with any relevant pharmacy data. As illustrated, such information gathering includes the steps of identifying the prescribing physician 400, identifying the medication prescribed 402, including the strength/dosage thereof. With respect to the latter, it is contemplated that the medication will be identified by name, daily dosage (when applicable), and the strength of the medication prescribed (e.g., famotidine 40 mg hs). Further pharmacy data to be documented include the quantity, such as the number of tablets prescribed to a specific patient and, in step 404, the date when such prescription is filled.

Comprehensively documenting all such information as part of the delivery of healthcare by PCP's to the patients they treat within the patient population will be operative to not only generate an extremely comprehensive, easily accessible, and easily updatable electronic medical record system, but will further enable the accuracy of the diagnoses to be assessed, as well as the appropriateness of the healthcare administered in relation thereto. To that end, and before discussing specific procedures followed in connection with the proper diagnosis of a patient having a chronic condition, the systems and methods of the present invention integrate a review step 110 that is operative to enable overseeing physicians, healthcare administrators, hospitalists or other knowledgeable individuals having a thorough understanding of the administration of healthcare to determine whether a submitted diagnosis and procedure/test rendered in response thereto is appropriate based upon a multiplicity of factors. In this regard, it is expressly contemplated that those practices disclosed and claimed in connection with Applicant's co-pending U.S. patent application Ser. No. 10/615,640 can be implemented to ensure that each of the PCP's administering healthcare to patients within the patient population are following a standardized protocol that strictly adheres to the delivery of quality, cost-effective healthcare.

As a further means of reviewing the PCP's performance in accurately diagnosing each specific condition for which each specific patient is treated, the systems and methods of the present invention may further incorporate the methodology of U.S. patent application Ser. No. 10/679,178, which incorporates a reference for standardized performance measures for rendering healthcare. Exemplary of such standards expressly include the National Committee for Quality Assurance's (NCQA) Healthplan Employer Data and Information Set (HEDIS), which is well-known and recognized in the art as a recognized standard for quality of healthcare and service that healthcare plans should attempt to provide to their members. Accordingly, such review of diagnosis and treatment, coupled with standardized treatment practices recognized in the art (as may be promulgated by consumer groups, government agencies, or healthcare administration agencies, including HEDIS standards discussed above), enables healthcare to be administered to the patients within the patient population according to recognized standards of care that can be continuously reviewed and updated.

To that end, the systems and methods of the present invention incorporate a further component, namely, component 112 shown in FIG. 1, that enables all of the diagnoses, treatment, lab tests, and prescription information outlined above to be compiled, assessed, and reviewed to ensure that the best medical management practices are followed, as well as how the delivery of healthcare can be administered as efficiently and cost-effectively as possible. In this respect, it is contemplated that a number of statistical techniques can be deployed to determine the rate of error by which one of more physicians improperly diagnoses a specific condition, perform an inappropriate procedure in response to a diagnosed condition, order wrong or unnecessary tests in response to a diagnosed condition, and/or prescribe medication that is either inappropriate, sub-therapeutic or improperly indicated to treat a specific condition. Along these lines, it is contemplated that all of the PCP's administering healthcare to the patient population can be continually reviewed and assessed for their performance to thus ensure that not only are the most cost-effective healthcare practices are being utilized, but to also improve physician judgment, eliminate wasteful practices, and that most cost-effective medical treatment is delivered. In this respect, it is expressly contemplated that the systems and methods of the present invention will achieve the dual purpose of conserving medical resources while at the same time improving the delivery of healthcare by ensuring that proper diagnosis, and hence appropriate procedures, tests, and medications prescribed in response thereto, are administered with little to no waste of resources.

In addition to the implementation of procedures to document and review the delivery of health care administered to a patient population, particularly with respect to the diagnosis of specific medical conditions and the procedures/tests performed in response thereto, the systems and methods of the present invention are particularly well suited for the cost-effective management of those patents within the patient population afflicted with high-cost chronic conditions. As discussed above in relation to FIGS. 1 and 2, as part of the diagnosis and treatment of each patient, each physician will identify, where appropriate, whether such patient is being treated for a high cost chronic condition, as identified in step 108 of FIGS. 1 and 204 of FIG. 2. Essentially, whether or not a patient is afflicted with a high-cost chronic condition will be determined by conventional medical evaluation and will encompass those specific chronic conditions specified in FIG. 5.

Presently, the present invention contemplates that high-cost chronic conditions can be identified as falling within at least eight (8) separate categories, namely cancer, cardiovascular disease, diabetes, dialysis condition, HIV/opportunistic infections, liver disease, pulmonary disease and quadriplegia/extensive paralysis. As further illustrated in FIG. 5, within each category of high-cost chronic conditions are specific medical conditions that are identified by a separate code. For example, for cancer, there are identified four (4) separate cancerous conditions, each of which having its own high-cost chronic condition (HCC) code. As shown, breast, prostate, colorectal cancers are identified as HCC 10; lung, upper digestive track and other sever cancers are identified as HCC 8; lymphatic, head and neck, brain cancers are identified as HCC 9; and metastatic cancer and acute leukemia are identified as HCC 7. Similar subcategories with their own dedicated HCC codes are further provided for each of the eight conditions. In this respect, it should be recognized that the HCC codes are exemplary of those that can be utilized in the coding practices utilized in the practice of the present invention. Such coding practice is significant insofar as the same not only reflect what should be the most accurate diagnosis of a patient, but in the case of a high-cost chronic condition, proper diagnosis is imperative to insure that the best, most comprehensive and cost-effective treatment can be delivered to the patient and that all relevant factors and disease progression are taken into consideration.

As part of such process, the initial step begins with confirming that a patient is in fact being treated for a high-cost chronic condition in 114. Such diagnosis is reviewed as part of such step to ensure that the diagnosis continues to accurately reflect the condition of the patient. Advantageously, such continuous review of the diagnosis ensures that the patient's condition is accurately characterized with the most appropriate treatment being utilized, as opposed to conventional wasteful practices where a chronic condition, once diagnosed, is treated indefinitely in a static, non-dynamic fashion which often time neglects to take into consideration related medical diagnosis and can result in suboptimal and even harmful care.

In addition to continuously reviewing the appropriateness of the high-cost chronic condition diagnosis, further assessment is made in step 116 with respect to any type of insurance claims submissions. As is well-known in the art, health care benefits are typically treated on an annual basis, with deductibles for which the patient is responsible for paying becoming due on the first of the calendar year. By virtue of the fact that such high-cost chronic conditions often times afflict patients for years, there is advantageously built into the systems and methods of the present invention procedures by which medical records are continuously updated so that to the extent insurance benefits are renewed periodically, such as a calendar year basis, all applicable information is necessary to insure ongoing coverage, benefits, and the like will be updated as part of step 116 such that a continuum of care cannot only be provided to the patient, but that the applicable benefits and coverage attendant thereto can be administratively tracked and reviewed. As is well-known in the art, to the extent such information is not timely updated, substantial administrative problems can occur which can require resubmission of claims information and potentially trigger the loss of certain benefits or otherwise trigger an obligation for the patient to pay higher deductibles, medical costs, and the like, which the patient would not otherwise be obligated to do but for accurate and timely diagnosis information that is properly updated.

In order to provide the most comprehensive care for such patients afflicted with a high-cost chronic condition, the present invention further takes into account potential medical complications associated with each specific high-cost chronic condition that enables the treating physicians to anticipate such potential complications and related diagnoses. As illustrated in step 118 of FIG. 1, there is integrated within the systems and methods of the present invention an on-going patient assessment whereby specific chronic conditions are reviewed to determine if further coding is required. In this respect, and as depicted in FIG. 6, a listing of the various chronic conditions will be provided and, preferably through a link provided as part of the electronic medical records for each patient, a series of pertinent clinical questions specific for each condition that must be taken into account by the treating physician in order to properly assess whether or not further coding is required for a given patient. For example, to the extent the patient has been diagnosed with cancer, when updating the electronic medical records for such patient the physician will be provided a quick reference to those questions identified in FIG. 7 that will direct the treating physician to continuously evaluate and assess the patient's condition and ultimately direct the physician to follow the proper medical protocol, through the coding practices referred to herein, to ensure that not only are further medical procedures and test warranted, but that the correct procedures and tests are prescribed and carried out in a timely manner to provide the best patient care possible. For example, in FIG. 7, to the extent a patient has been diagnosed with cancer, the treating physician will necessarily be prompted to review each of the questions identified, such as whether or not the patient has been actively managed for malignant neoplasms and whether the medical records for such patient contained documentation of active treatment for pulmonary or disseminated micro bacteria, among others. To the extent a patient does have a specific type of condition, such as a malignant neoplasm of the prostate or if the patient has malignant breast cancer, additional coding may be required to provide adequate care to the patient. Advantageously, by utilizing the extremely comprehensive collection of data discussed above enables the patient's condition to be thoroughly assessed to not only provide the most practical health care but to also substantially minimize, if not eliminate, potential liability for a misdiagnosis and improper patient documentation.

Referring now to FIGS. 8-10, there is illustrated those clinical questions that must be asked for those patients properly diagnosed of other types of high-cost chronic conditions. In FIG. 8, there is illustrated the questions linked to cardiovascular disease which every physician must review for each patient properly diagnosed with such condition. As illustrated, the treating physician must take into consideration whether the patient has prior history of cardiopulmonary disorder predisposing to current cardiac issues and whether the patient meets clinical criteria for cardiomyopathy, among other considerations. Also, to the extent atrial or ventricular arrhythmia is diagnosed, specific coding is essential to ensure that the appropriate on-going medical diagnosis, treatment and tests are prescribed.

FIG. 9 represents those considerations that must be made to the extent the patient is properly diagnosed with a dialysis condition. As illustrated, physicians must take into consideration whether or not the patient was receiving accurate treatment for chronic renal failure, chronic uremia, and other conditions while the patient had previously been treated. Likewise, FIG. 10 depicts those questions that the physician is directed to and is to take into consideration to the extent that the patient has been properly diagnosed with either HIV or an opportunistic infection. For example, a treating physician must necessarily review and determine whether or not the patient has previously been treated for candidal pneumonia, *aspergillous* species, or other types of infections attendant to the underlying treatment of the patient's chronic condition.

With respect to the further coding that must be taken into consideration as illustrated in FIGS. 6-10, it will be understood by those skilled in the art that the specific questions and further medical assessment that the physician will be prompted to take into consideration will be continuously updated as improvements are made in medicine regarding patient diagnosis and treatment. It is likewise contemplated that additional high-cost chronic conditions may be added to those identified in FIG. 6 and that for each such additional chronic condition, a subset of the questions and clinical treatment considerations will be identified using known, objective diagnostic standards that will be agreed upon by the medical community as providing a standard that all treating physicians should follow according to best patient management practices. Accordingly, the specific questions and considerations set forth in FIGS. 7-10 are merely illustrative of the further considerations that are made with present best medical management practices.

As a further consideration to be documented as part of the administration of care to patients with high-cost chronic conditions, the treating physician will further identify whether or not the patient afflicted with the high-cost chronic condition is adjudged to have either a low, medium or high risk as part of step 118. Along these lines, and as is well-known to those skilled in the art, the severity of a given condition can be readily assessed, and the present invention takes such risk into consideration so that the aggressiveness of medical treatment can be proportionately tailored to address the same. The assignment of risk will be periodically updated and reviewed for accuracy. To the extent a patient is properly identified as being a higher risk patient, it will be understood that more aggressive measures may be taken should a favorable patient outcome be reasonably anticipated. On the other hand, designating such a patient as high risk, depending on the circumstances, may warrant that only palliative measures be taken to thus not only conserve medical resources, but to also treat the patient as realistically as practical.

In addition to continuous review of diagnosis, risk assessment, claims updating and review of the patients' conditions to determine whether or not further coding is appropriate, the present invention further includes a component, identified as 120 of FIG. 1, that involves determining whether or not a given high-cost chronic condition progresses to a further stage requiring additional diagnosis. Specifically, patients that have been properly diagnosed with a high-cost chronic condition will further be continuously reviewed for potential additional related diagnosis. As explained in connection with FIGS. 5 and 11, there is illustrated the specific high-cost chronic conditions by specific HCC codes in FIG. 5 and how those patients diagnosed with such specific conditions will be reassessed by the treating physicians to determine whether or not an additional related diagnosis identified in FIG. 11 must also be made. For example, patients diagnosed with a high-cost chronic condition code HCC 8, such as lung cancer for example, will further be reviewed by the treating physician to determine whether or not the patient should further be diagnosed with HCC 7, namely metastatic cancer. Similarly, patients diagnosed with diabetes with acute complications, HCC 17, will be reviewed to determine whether or not a diagnosis of diabetes with neurologic manifestation HCC 16 or diabetes with peripheral circulatory manifestation HCC 15 are justified as additional related diagnoses. Such review will be continuously documented as part of the patient's medical records The review for potential additional related diagnoses will be consistent with objective, standardized medical management practices, and may change from time to time as such medical practices change in the art. With respect to the additional related diagnosis identified in FIG. 11, it will thus be understood that the same may change or become modified over time as such medical practices dictate. Advantageously, by taking such related diagnoses into account, the practices of the present invention enable a patient's condition to be dynamically treated, especially if the disease progresses on to the related conditions identified. For example, patients with chronic hepatitis, HCC 27 or cirrhosis of the liver HCC 26, will be continuously monitored to determine whether or not the patient ultimately progresses to end-stage liver disease HCC 25. All medically appropriate procedures and tests can thus accordingly be assigned to such patient as the patient's disease evolves, which in turn allows for the most applicable medical treatment in conservation of medical resources.

The systems and methods of the present invention further include, as part of such comprehensive diagnosis, treatment, review and documentation of patients with high-cost chronic conditions, a review component 122 that, per the practices discussed above, ensure that the treating physicians are delivering the most appropriate, objectively-reasonable health care as may be reviewed by knowledgeable hospitalists, administrators, health care workers, and the like. Along these lines, such review component plays an important role in the management of high-cost chronic conditions insofar as those patients properly diagnosed with high-cost chronic conditions often times utilize vastly more medical resources and require substantially greater care for longer periods of time than the vast majority of the patients within the patient population. Accordingly, one of the major objectives of the present invention is to provide a tool operative to contain costs in delivering health care to a patient population and by integrating such review step allows not only for the best standard of care to be administered utilizing objective criteria, but also be delivered in extremely efficient and cost effective manner.

To that end, the present invention, by focusing on delivering such cost effective health care for the treatment of those patients afflicted with a high-cost chronic condition, enables those patients to be readily identified in optional step 124 to define a subpopulation whose information can be readily accessed, reviewed and scrutinized to determine whether or not the best most efficient medical practices are being followed. Identifying such patient population can be of additional use in assessing the epidemiology and etiology of specific diseases and medical conditions.

Additional modifications and improvements of the present invention will be apparent to those of ordinary skill in the art. Along these lines, the systems and methods of the present invention can be implemented as part of virtually any health care delivery system, including any conventional public or private system, such as a health maintenance organization, health plan or government sponsored program, that is responsible for overseeing the utilization of health care resources of an integrated delivery system to administer health care to a patient population. If implemented correctly, the systems and methods of the present invention can optimally administer and substantially conserve the utilization of health care resources to thus enable high-quality and objectively verifiable health care to be delivered while at the same time enabling cost-effective services to be rendered. Indeed, it is contemplated that the health care administration systems and methods of the present invention can and will serve as a model from which existing health care administration systems can and emulate to not only conserve resources, but where applicable, substantially increase profitability and improve patient outcomes.

Moreover, the system of the present invention, while advantageously preserving the interests of privacy and security related information, may further be useful in facilitating standardized electronic transactions, consistent with the mandate of HIPAA, as well as collecting information useful for research. In this respect, the system of the present invention will be operative to obtain information related to a specific medical practice, hospital, or type of care provided in a general area, which may be extremely useful in predicting trends and anticipating future healthcare needs. In this regard, information related to hospital admissions, type and nature of medical procedures or services rendered by a specific medical practitioner or medical group, type and volume of prescription medications that are prescribed by a specific physician or medical group, and information related generally to the diagnosis and clinical evaluation made by a practitioner or medical group can be compiled through the system of the present invention and useful in assessing the epidemiology and etiology of a specific disease or abnormal condition. Furthermore, in certain limited applications, the data created by the system of present invention may be useful as marketing data which can be utilized to determine the practice characteristics of a specific practitioner or health group. Exemplary of the latter includes prescribing habits, particularly with respect to volume and types of medication prescribed by a given practitioner, which is extremely useful as marketing data for determining sales effectiveness, market share, and trends in medical management practices.

Accordingly, the particular combination of parts and steps described and illustrated herein will be understood to represent only certain embodiments of the present invention, and are not intended to serve as limitations of alternative systems and methods falling within the scope of the present invention.

What is claimed is:

1. A method of treating high-cost chronic conditions, the method comprising:
    compiling, on an electronic database using medical record software, electronic medical records for a plurality of patients, the medical record for each individual patient defining one or more treating physicians associated with the treatment of that individual patient and including a claims history tracking each event for which medical care was rendered, the patient's case management, pharmacy information related to all medications prescribed to the patient, and all laboratory tests and results therefrom, including the specific dates that such procedures and tests were performed and medications prescribed;
    making the compiled electronic medical records accessible over the Internet via a secure web-based system, the secure web-based system providing a secure means by which the compiled electronic medical records can be generated, stored, retrieved, and reviewed;
    securely facilitating standardized electronic transactions on the secure web-based system according to a standardized transaction format using the electronic medical records, the standardized electronic transactions including claims, remittance and payment advice, claims status, enrollment and disenrollment in a health plan, premium payments, eligibility inquiries and responses, referral certifications and authorizations, and coordination of benefits;
    identifying, on the electronic database, a subpopulation among the plurality of patients, the subpopulation being identified based upon the electronic medical records indicating an affliction with a high-cost chronic condition from among cancer, cardiovascular disease, diabetes, dialysis condition, HIV/opportunistic infections, liver disease, pulmonary disease, and quadriplegia/extensive paralysis;

for each of the individual patients who are not part of the identified subpopulation, reviewing the compiled electronic medical records for the patient for conformance with a standardized coding practice, the standardized coding practice including International Classification of Diseases (ICD) codes identifying medical diagnoses and Current Procedural Terminology (CPT) codes identifying healthcare services;

for each of the individual patients of the identified subpopulation, continuously reviewing whether the compiled electronic medical records indicate the affliction with the high-cost chronic condition;

generating, on the secure web-based system, a plurality of links corresponding to the electronic medical records for each respective patient of the identified subpopulation, each of the links providing access to a series of pertinent clinical questions specific to a condition associated with the respective patient;

prompting the one or more treating physicians to review each of the questions using the secure web-based system;

assessing, on the electronic database, for each of the individual patients of the identified subpopulation, a diagnostic risk factor indicating the severity of diagnosis as being low, medium, or high risk, the assessing being performed via comparison of the electronic medical records of the individual patients to identified, objective diagnostic standards;

periodically updating and reviewing the diagnostic risk factor for each of the individual patients of the identified subpopulation;

determining, on the electronic database, for each of the individual patients of the identified subpopulation, a treatment aggressiveness factor indicating the aggressiveness of medical treatment pursued, the treatment aggressiveness factor being determined via comparison of the electronic medical records of the individual patients with identified, objective treatment standards;

assigning, on the database, to the one or more treating physicians associated with the treatment of each individual patient, a treatment score, the treatment score being assigned based upon the correlation between the assessed diagnostic risk factor and the determined treatment aggressiveness factor;

generating, through the use of a statistical ruleset on the database, a treating physician performance metric for each treating physician, the treating physician performance metric in each of diagnosing a specific condition, performing an inappropriate procedure in response to a diagnosed condition, ordering wrong or unnecessary tests in response to a diagnosed condition, and prescribing medication that is either inappropriate, sub-therapeutic or improperly indicated to treat a specific condition;

generating a set of output data which indicates the rates of error by treating physician, the set of output data indicating an aggregate of the disparity between the diagnosed specific condition and an actual specific condition of the individual patient, the wrong or unnecessary tests in response to a diagnosed condition and the correct tests in response to a diagnosed condition, and the prescribed medication that is either inappropriate, sub-therapeutic or improperly indicated to treat a specific condition and prescribed medication that is correctly prescribed; and administering a medical treatment to a patient from among the individual patients of the identified subpopulation, the medical treatment being determined at least in part based on the assessed diagnostic risk factor.

2. The method of claim 1, wherein the medical records for each individual patient additionally defines a treating facility, and wherein a treatment score is additionally assigned to each treating facility, with the database additionally generating a treating facility performance metric for each treating facility based upon the aggregate of the treatment scores assigned to that treating facility.

3. The method of claim 1, wherein the medical records for each additional patient additionally defines a testing laboratory, and wherein a treatment score is additionally assigned to each testing laboratory, with the database additionally generating a testing laboratory performance metric for each testing laboratory based upon the aggregate of the treatment scores assigned to that testing laboratory.

4. The method of claim 1, wherein the medical records for each additional patient additionally defines a pharmacy, and wherein a treatment score is additionally assigned to each pharmacy, with the database additionally generating a pharmacy performance metric for each pharmacy based upon the aggregate of the treatment scores assigned to that pharmacy.

* * * * *